US012661444B2

(12) United States Patent
Arnett

(10) Patent No.: US 12,661,444 B2
(45) Date of Patent: Jun. 23, 2026

(54) DRUG CONTAINER SYSTEMS INCLUDING LOCK-OUT MECHANISMS

(71) Applicant: Eli Lilly and Company, Indianapolis, IN (US)

(72) Inventor: Jaime Ray Arnett, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 945 days.

(21) Appl. No.: 17/796,006

(22) PCT Filed: Jan. 29, 2021

(86) PCT No.: PCT/US2021/015657
§ 371 (c)(1),
(2) Date: Jul. 28, 2022

(87) PCT Pub. No.: WO2021/158434
PCT Pub. Date: Aug. 12, 2021

(65) Prior Publication Data
US 2023/0051213 A1 Feb. 16, 2023

Related U.S. Application Data

(60) Provisional application No. 62/970,814, filed on Feb. 6, 2020.

(51) Int. Cl.
*A61M 5/00* (2006.01)
*A61M 5/50* (2006.01)

(52) U.S. Cl.
CPC .............. *A61M 5/002* (2013.01); *A61M 5/50* (2013.01)

(58) Field of Classification Search
CPC .... A61M 5/002; A61M 5/50; A61M 2209/06; A61M 2205/273; A61M 5/31535;
(Continued)

(56) References Cited

U.S. PATENT DOCUMENTS 3,934,722 A * 1/1976 Goldberg ............... B65D 41/32
215/253
7,004,349 B2 2/2006 Heiberg et al.
(Continued)

FOREIGN PATENT DOCUMENTS

CN 206167538 U * 5/2017 .............. A61M 5/50
EP 2835146 2/2015
(Continued)

OTHER PUBLICATIONS

Patent Cooperation Treaty International Search Report pertaining to International Application No. PCT/US2021/015657; International Filing Date: Jan. 29, 2021; Date of Mailing: May 17, 2021.
(Continued)

*Primary Examiner* — Cris L. Rodriguez
(74) *Attorney, Agent, or Firm* — M. Daniel Spillman

(57) ABSTRACT

A drug delivery system includes a drug delivery device that carries and delivers a drug. The system further includes a housing, and the housing includes a main body and a cover coupled to the main body. The main body includes a chamber that carries the drug delivery device and an opening coupled to the chamber. The cover is movable relative to the main body from a closed position to an open position. In the closed position the cover obscures the opening and thereby inhibits egress of the drug delivery device from the chamber via the opening, and in the open position the cover permits egress of the drug delivery device from the chamber via the opening. A lock-out mechanism is carried by the housing. The lock-out mechanism inhibits the cover from returning to the closed position after moving to the open position.

15 Claims, 10 Drawing Sheets

(58) Field of Classification Search
  CPC .......... A61M 5/31538; A61M 5/31591; A61M
      2005/3217; A61M 15/0026; B65D 43/24;
      B65D 43/2251; B65D 43/1008
  USPC ................................................ 220/832, 831
  See application file for complete search history.

(56)                    References Cited

U.S. PATENT DOCUMENTS

| 10,765,602 | B1 * | 9/2020 | Arnett | ................. | B05B 11/0027 |
| 2012/0016300 | A1 * | 1/2012 | Ruan | ................... | A61M 5/5086 |
| | | | | | 604/110 |
| 2012/0041380 | A1 * | 2/2012 | Chapin | ............... | A61M 5/3202 |
| | | | | | 206/365 |
| 2014/0367288 | A1 * | 12/2014 | Ziegner | ................. | A61M 5/002 |
| | | | | | 206/366 |
| 2018/0001015 | A1 * | 1/2018 | Ziegner | ............... | B65D 83/766 |
| 2021/0170140 | A1 * | 6/2021 | Owen | ................. | A61M 25/002 |
| 2022/0288299 | A1 * | 9/2022 | Limaye | ................. | A61M 5/002 |
| 2025/0134771 | A1 * | 5/2025 | Klein | ................... | B65D 43/162 |

FOREIGN PATENT DOCUMENTS

| WO | WO-2016168400 | A1 * | 10/2016 | ............. | G16H 20/13 |
| WO | 2020204991 | | 10/2020 | | |

OTHER PUBLICATIONS

Patent Cooperation Treaty Written Opinion of the International
Searching Authority pertaining to International Application No.
PCT/US2021/015657; International Filing Date: Jan. 29, 2021;
Date of Mailing: May 17, 2021.

* cited by examiner

DRUG CONTAINER SYSTEMS INCLUDING LOCK-OUT MECHANISMS

FIELD OF THE DISCLOSURE

The present disclosure relates to drug delivery systems, and in particular, to drug delivery systems including single-use drug delivery devices, housings for initially carrying the drug delivery devices, and lock-out mechanisms for inhibiting replacement of the drug delivery devices in the housings after use.

BACKGROUND

Drug delivery devices are typically initially stored or carried in protective housings, and the devices are typically removed from the housings when drugs or medications are to be administered to individuals (for example, during emergency situations). Some drug delivery devices only carry a single dose of a drug (and, as such, may be referred to as "single-use" devices). Such devices should be discarded after use, although such devices may be mistakenly returned to a housing after use. It may be confusing or problematic if it is not recognized that a drug delivery device has already been used and its drug supply has been depleted.

SUMMARY

According to an embodiment of the present disclosure, a drug delivery system includes a drug delivery device that carries and is configured to deliver a drug. The system further includes a housing, and the housing includes a main body and a cover coupled to the main body. The main body includes a chamber that carries the drug delivery device and an opening coupled to the chamber. The cover is movable relative to the main body from a closed position to an open position. In the closed position the cover obscures the opening and thereby inhibits egress of the drug delivery device from the chamber via the opening, and in the open position the cover permits egress of the drug delivery device from the chamber via the opening. A lock-out mechanism is carried by the housing. The lock-out mechanism is configured to inhibit the cover from returning to the closed position after moving to the open position.

According to another embodiment of the present disclosure, a drug delivery system includes a drug delivery device that carries and is configured to deliver a drug. The system further includes a housing having a first housing portion and a second housing portion coupled to the first housing portion. The first housing portion includes a chamber carrying the drug delivery device and an opening coupled to the chamber. The second housing portion initially obscures the opening and thereby inhibits egress of the drug delivery device from the chamber via the opening. The second housing portion is movable relative to the first housing portion to open the housing and permit egress of the drug delivery device from the chamber via the opening. A lock-out mechanism carried is by the housing, and the lock-out mechanism is configured to inhibit the housing from reclosing after being opened.

According to yet another embodiment of the present disclosure, a drug delivery system includes a drug delivery device that carries and is configured to deliver a drug. The system further includes a housing, and the housing includes a main body and a cover coupled to the main body. The main body includes a chamber carrying the drug delivery device and an opening coupled to the chamber. The cover is movable relative to the main body from a closed position to an open position. In the closed position the cover obscures the opening and thereby inhibits egress of the drug delivery device from the chamber via the opening, and in the open position the cover permits egress of the drug delivery device from the chamber via the opening. A lock-out mechanism is carried by the housing. The lock-out mechanism is movable from an initial position to a lock-out position. The lock-out mechanism occupies the initial position when the cover occupies the closed position, the lock-out mechanism occupies the lock-out position when the cover occupies the open position. In the lock-out position the lock-out mechanism causes one of the drug delivery device and the lock-out mechanism to be disposed outwardly of the housing and thereby inhibits the cover from returning to the closed position.

BRIEF DESCRIPTION OF THE DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

Figures 1, 2:
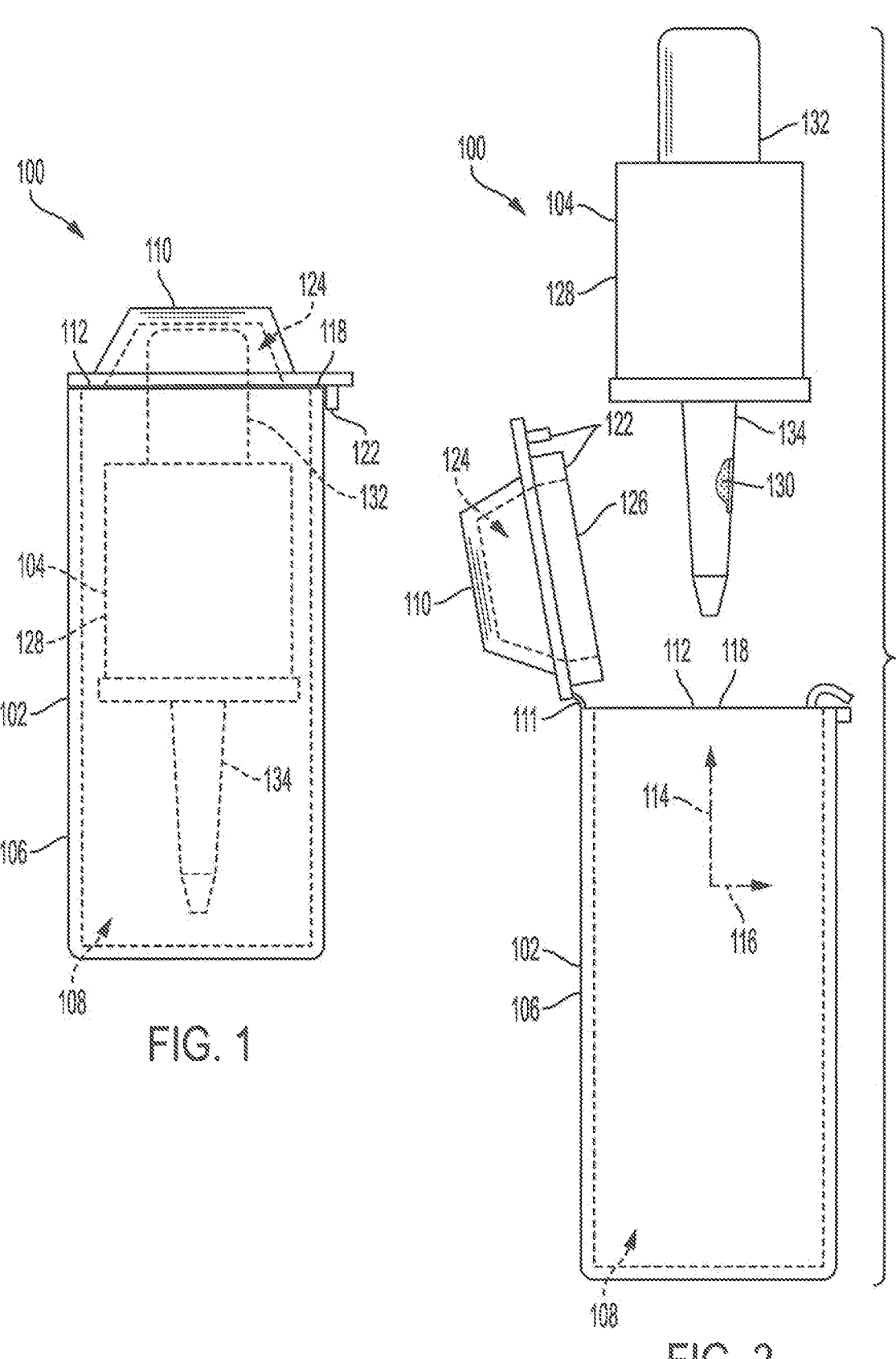
FIG. 1 is a side view of a first embodiment of a drug delivery system according to the present disclosure; several internal components are illustrated with phantom lines; a cover is shown coupled to a main body of a housing and a drug delivery device is shown carried within a chamber of the housing.
FIG. 2 is another side view of the drug delivery system of FIG. 1; the cover is shown detached from the main body and the drug delivery device is shown removed from the housing.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

As described in further detail below, drug delivery systems according to some embodiments of the present disclosure include lock-out mechanisms that advantageously inhibit drug delivery devices from being replaced in housings after use.

FIGS. 1 and 2 illustrate a drug delivery system 100 according to an embodiment of the present disclosure. The drug delivery system 100 generally includes a housing 102 that initially carries a drug delivery device 104. The housing 102 includes a main body 106, which may also be referred to as a first housing portion. The main body 106 includes a main chamber 108 that initially receives the drug delivery device 104. The housing 102 further includes a cover 110, which may also be referred to as a second housing portion. As illustrated in FIG. 1, the cover 110 initially obscures a main opening 112 coupled to the main chamber 108 of the main body 106. As such, the cover 110 initially inhibits egress of the drug delivery device 104 from the main chamber 108 via the main opening 112. Stated another way, in a closed position the cover 110 couples to the main body 106 to obscure the main opening 112 and thereby inhibit egress of the drug delivery device 104 from the main chamber 108 via the main opening 112. As illustrated in FIG. 2, the cover 110 may be moved relative to the main body 106 and apart from the main opening 112 to permit egress of the drug delivery device 104 from the main chamber 108 via the main opening 112. Stated another way, in an open position the cover 110 is disposed apart from the main opening 112 to permit egress of the drug delivery device 104 from the main chamber 108 via the main opening 112.

In some embodiments and as illustrated, the main body 106 has a generally tubular or cylindrical shape that defines a longitudinal axis 114 and a perpendicular radial direction 116. The main opening 112 may be disposed at an end 118 of the main body 106 disposed along the longitudinal axis 114, and the drug delivery device 104 may thereby enter and exit the main chamber 108 of the main body 106 by translating along the longitudinal axis 114. In alternative embodiments, the main body 106 may have other shapes.

In some embodiments and as illustrated, the cover 110 includes a plurality of latching features 122 to facilitate initially coupling to the main body 106. The latching features 122 facilitate detachably coupling to the cover 110 to the main body 106. In some embodiments, the cover 110 may couple to the main body 106 in additional manners or other manners. As a specific example and as illustrated, the cover 110 may hingedly couple to the main body 106 via a hinge 111 (see FIG. 2). In some embodiments and as illustrated, the cover 110 includes a cover chamber 124 that is initially coupled to the main opening 112 and the main chamber 108 of the main body 106. The cover chamber 124 may initially receive the drug delivery device 104 together with the main chamber 108. The cover 110 may also include a cover opening 126 (FIG. 2) coupled to the cover chamber 124. In other embodiments, the cover 110 may lack the cover chamber 124 and the cover opening 126.

With continued reference to FIGS. 1 and 2, the drug delivery device 104 may be a single-use device that generally includes a device body 128 and a trigger or plunger 132 operable to cause the drug device 104 to discharge a drug 130 (FIG. 2) carried in a discharge element 134, which may also be referred to as a nozzle. As a more specific example, the drug 130 may be a powder-based drug, and the trigger 132 may be operable to increase pressure within the drug delivery device 104 to facilitate discharging the drug 130 from the discharge element 130. The drug delivery device 104 is illustratively shown as being an intranasal device for delivering a powder-based drug to treat hypoglycemia, such as glucagon. However, drug delivery devices according to embodiments of the present disclosure may take various other forms, such as an injector device for delivering a liquid-based drug to treat anaphylaxis, such as epinephrine, or an oral inhaler device for delivering an aerosol-based drug to treat asthma exacerbation, such as a bronchodilator.

Figure 4:
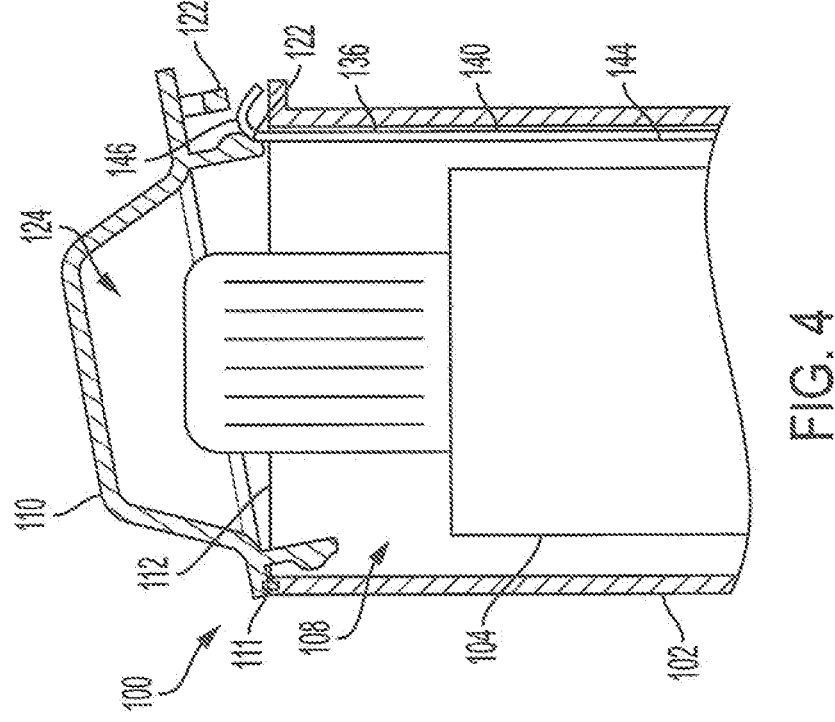
FIG. 4 is another partial longitudinal section side view of the drug delivery system of FIG. 1; the cover is shown partially detached from the main body and the lock-out mechanism is shown inhibiting reclosure of the housing.
Figure 3:
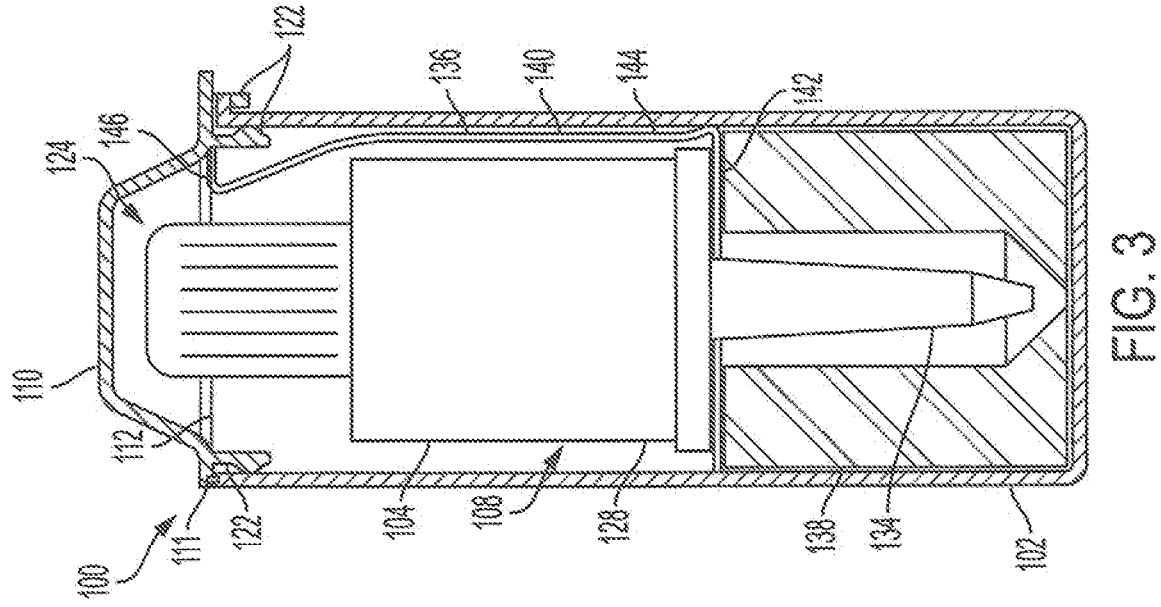
FIG. 3 is a partial longitudinal section side view of the drug delivery system of FIG. 1; the cover is shown coupled to the main body, and the drug delivery device and a lock-out mechanism are shown carried within the chamber of the housing.

FIGS. 3 and 4 illustrate the drug delivery system 100 in partial longitudinal section such that several internal components are visible, including the drug delivery device 104 and a lock-out mechanism 136 that inhibits reclosing the drug delivery system 100. The housing 102 also illustratively carries a desiccant element 138 within the main chamber 108 and proximate the discharge element 134 of the drug delivery device 104. In one embodiment, the desiccant element 138 is in an annular shape defining a bore extending axially therein. The bore is configured to receive a portion of the device 104. In one embodiment, the bore may be shaped to correspond generally to the outline shape of a portion of the device 104, such as, for example, the discharge element 134. The lock-out mechanism 136 includes a resilient member 140 that is generally a thin component formed of one or more materials providing resiliency characteristics, such as metals, plastics, or the like. The resilient member 140 includes a radially-extending foot portion 142 (FIG. 3) disposed between the device body 128 and the desiccant element 138. The foot portion 142 couples to a generally longitudinally-extending spine portion 144, which in turn couples to a generally radially-extending arm portion 146 disposed near the main opening 112 of the main chamber 108. In this way, the resilient member 140 is generally Z-shaped.

As illustrated in FIG. 3, the arm portion 146 of the resilient member 140 initially engages the cover 110 within the cover chamber 124. Stated another way, the resilient member 140 occupies an initial position in which the arm portion 146 engages the cover 110 within the cover chamber 124 when the cover 110 occupies the closed position. In the initial position, the arm portion 146 and/or the spine portion 144 deflect and store energy. Stated another way, the resilient member 140 is loaded in the initial position. In this illustrated initial position of FIG. 3, the latching features 122 of the cover 110 are free to engage and couple to the main body 106 without interference from the arm portion 146.

As illustrated in FIG. 4, when the cover 110 moves from the closed position to the open position, the resilient member 140 disengages the cover 110 and moves to a lock-out position. Stated another way, the resilient member 140 releases stored energy, or is unloaded (as used herein, meaning less loaded relative to the initial position), to move to the lock-out position. In the lock-out position, the arm portion 146 of the resilient member 140 is disposed longi-tudinally and radially outwardly of main chamber 108. As a result, the arm portion 146 inhibits and/or discourages reclosing the housing 102, or moving the cover 110 from the open position to the closed position, for example, after removal of the drug delivery device 104 from the housing 102 and use of the drug delivery device 104. In this illustrated lock-out position of FIG. 4, the arm portion 146 protrudes radially outward to interfere with the connection between the latching features 122 of the cover 110 and the main body 106.

Figure 6:
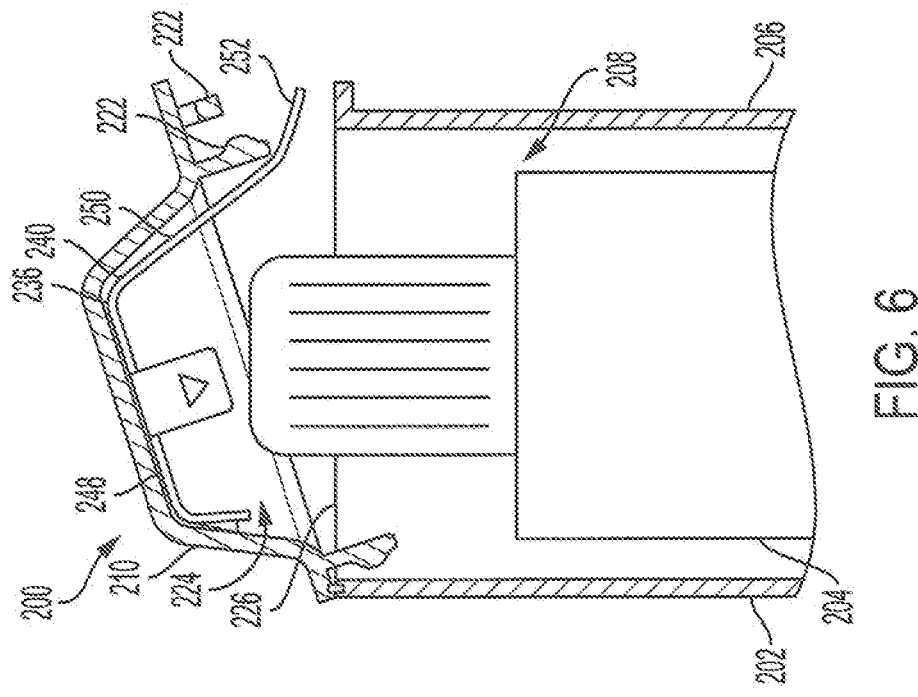
FIG. 6 is another partial longitudinal section side view of the drug delivery system of FIG. 5; the cover is shown partially detached from the main body and the lock-out mechanism is shown inhibiting reclosure of the housing.
Figure 5:
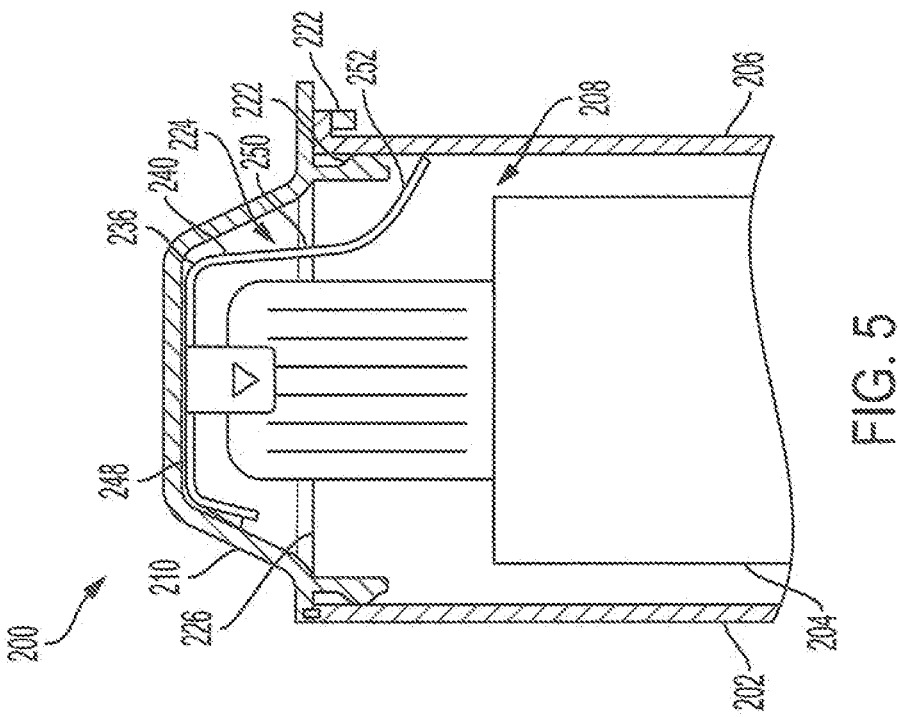
FIG. 5 is a partial longitudinal section side view of a second embodiment of a drug delivery system according to the present disclosure; a cover is shown coupled to a main body of a housing, and a drug delivery device and a lock-out mechanism are shown carried within a chamber of the housing.

FIGS. 5 and 6 illustrate a drug delivery system 200, in partial longitudinal section, according to another embodi-ment of the present disclosure. The drug delivery system 200 includes a housing 202 and a drug delivery device 204, which may be similar or identical to the housing 102 and the drug delivery device 104 described above, respectively. The drug delivery system 200 also includes a lock-out mecha-nism 236 that is generally carried within the cover chamber 224. The lock-out mechanism 236 includes a resilient mem-ber 240 that is generally a thin component formed of one or more materials providing resiliency characteristics, such as metals, plastics, or the like. The resilient member 240 includes a head portion 248 that couples to the cover 210, as described in further detail below. The head portion 248 couples to a generally longitudinally-extending spine por-tion 250, which in turn couples to a generally radially-extending toe portion 252 disposed near the cover opening 226.

As illustrated in FIG. 5, the toe portion 252 of the resilient member 240 initially engages the main body 206 of the housing 202 within the main chamber 208. Stated another way, the resilient member 240 occupies an initial position in which the toe portion 252 engages the main body 206 within the main chamber 208 when the cover 210 occupies the closed position. In the initial position, the toe portion 252 and/or the spine portion 250 deflect and store energy. Stated another way, the resilient member 240 is loaded in the initial position. In this illustrated initial position of FIG. 5, the latching features 222 of the cover 210 are free to engage and couple to the main body 206 without interference from the toe portion 252.

As illustrated in FIG. 6, when the cover 210 moves from the closed position to the open position, the resilient member 240 disengages the main body 206 and moves to a lock-out position. Stated another way, the resilient member 240 releases stored energy, or is unloaded, to move to the lock-out position. In the lock-out position, the toe portion 252 of the resilient member 240 is disposed longitudinally and radially outwardly of main chamber 208. As a result, the toe portion 252 inhibits and/or discourages reclosing the housing 202, or moving the cover 210 from the open position to the closed position, for example, after removal of the drug delivery device 204 from the housing 202 and use of the drug delivery device 204. In this illustrated lock-out position of FIG. 6, the toe portion 252 protrudes radially outward to interfere with the connection between the latch-ing features 222 of the cover 210 and the main body 206.

Figure 7:
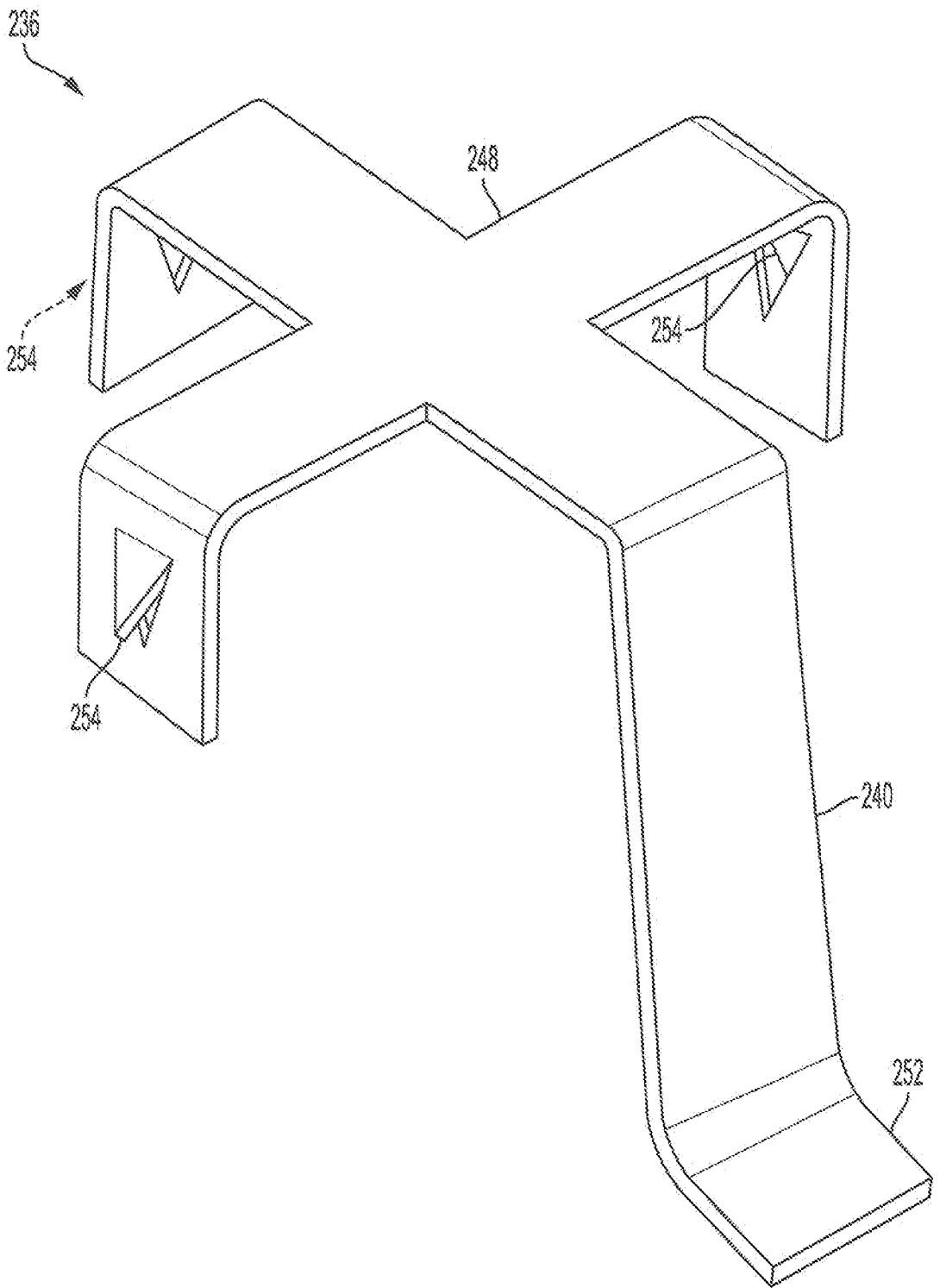
FIG. 7 is a perspective view of a lock-out mechanism of the drug delivery system of FIG. 5.

FIG. 7 illustrates a perspective view of the lock-out mechanism 236. The head portion 248 of the lock-out mechanism 236 illustratively includes a plurality of coupling features, specifically a plurality of protruding barbs 254, for coupling the lock-out mechanism 236 to the cover 210 (shown in FIGS. 5 and 6).

In various embodiments of drug delivery systems accord-ing to the present disclosure, including the drug delivery system 100 and the drug delivery system 200, the systems may be assembled, in part, by using a relatively thin tool or fixture to move the resilient member toward the initial position and quickly closing the cover such that the resilient member engages the inside of the cover and occupies the initial position. In other embodiments, including the embodiment described below, systems may include compo-nents that facilitate using different assembly processes.

Figure 8:
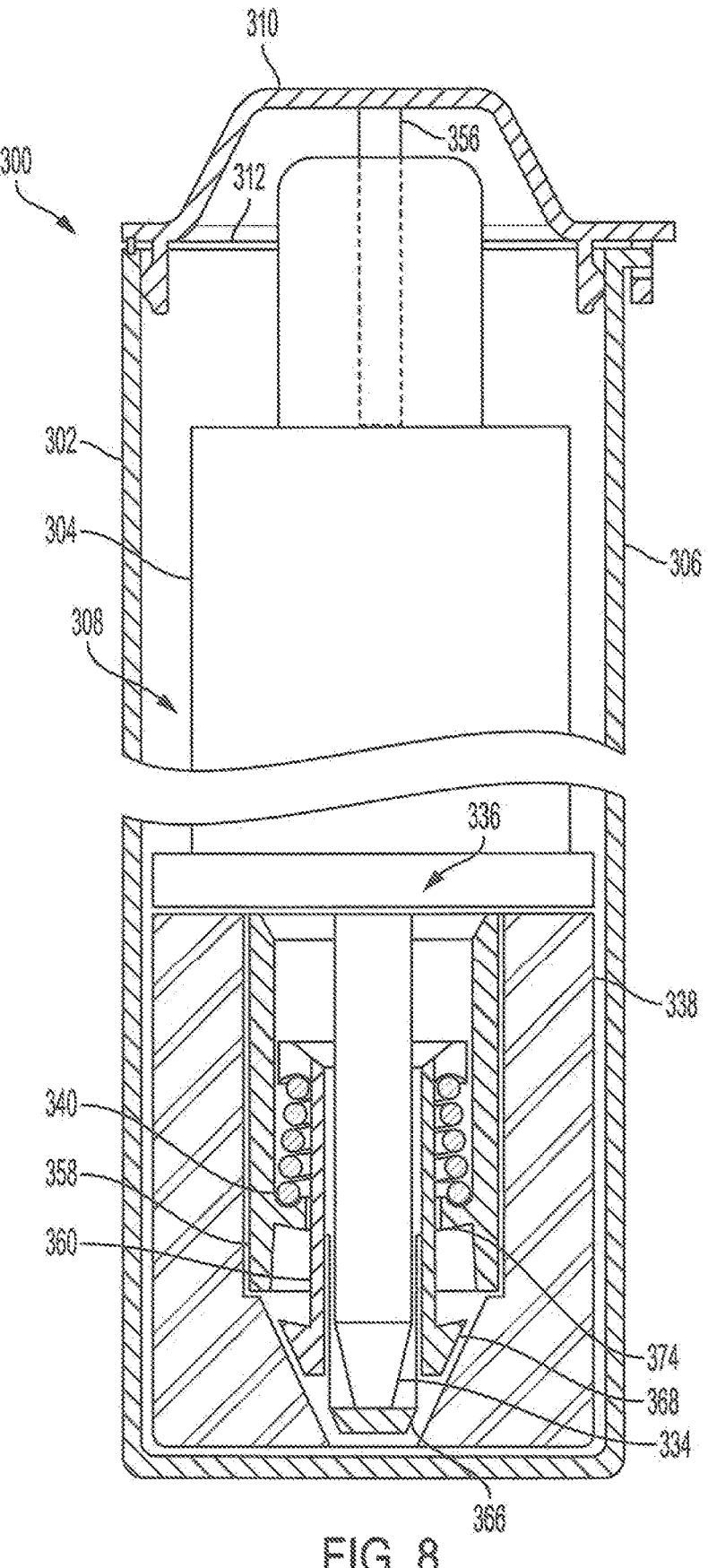
FIG. 8 is a partial longitudinal section side view of a third embodiment of a drug delivery system according to the present disclosure; a cover is shown coupled to a main body of a housing, and a drug delivery device is shown carried within a chamber of the housing.

FIG. 8 illustrates a drug delivery system 300, in partial longitudinal section, according to yet another embodiment of the present disclosure. The drug delivery system 300 includes a housing 302 and a drug delivery device 304, which may be similar or identical to the housing 102 and the drug delivery device 104 described above, respectively, except that the cover 310 includes a plurality of longitudi-nally-extending ribs 356, one of which is shown in FIG. 8, for engaging the drug delivery device 304 as described in further detail below. The drug delivery system 300 also includes a lock-out mechanism 336 that is generally carried within the desiccant element 338 and surrounds the dis-charge element 334. The lock-out mechanism 336 generally includes a shuttle holder 358 coupled to the desiccant element 338, a shuttle 360 that translates relative to the shuttle holder 358 and couples to the discharge element 334 of the drug delivery device 304, and a resilient member 340, illustratively a compression spring, coupling the shuttle holder 358 to the shuttle 360. The resilient member 340 urges the shuttle 360 and the drug delivery device 304 toward the main opening 312 of the housing 302. These aspects are described in further detail below. The shuttle holder 358 is coupled to the desiccant element 338 such that shuttle holder 358 and desiccant element 338 are at least one of rotationally locked and axially locked with one another, even though a gap is shown between the components for illustrative purposes only. In one example, the outer radial surface of shuttle holder 358 that has a cylindrical shape couples to the interior surface defined by the bore that is formed in the desiccant element 338 via a radial interference fit, although other coupling mechanism may be utilized such as, for example, adhesive, threaded engagement, pin/slot engagement between the two components. In one embodi-ment, the portion of the drug delivery device, such as the discharge element 334 and the shuttle holder 358 are in a coaxial relationship, and/or the shuttle holder 358 is at least one of rotationally and axially locked relative to the desic-cant element 338.

Figure 9:
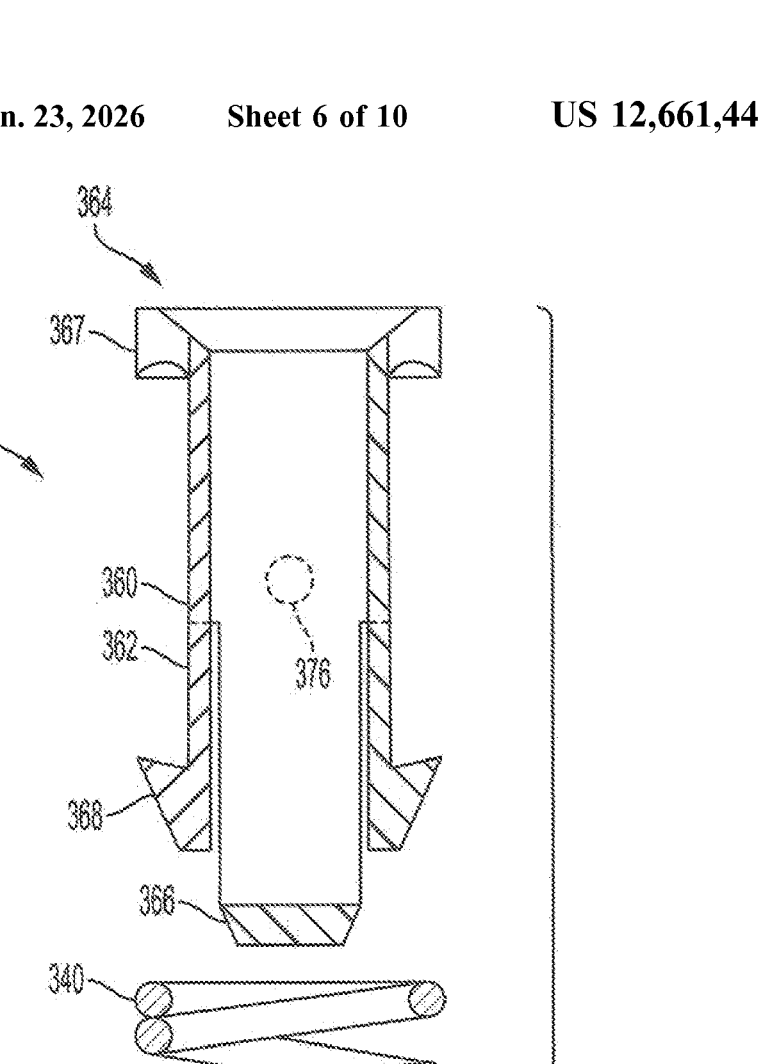
FIG. 9 is an exploded partial longitudinal section side view of a lock-out mechanism of the drug delivery system of FIG. 8.
Figure 9:
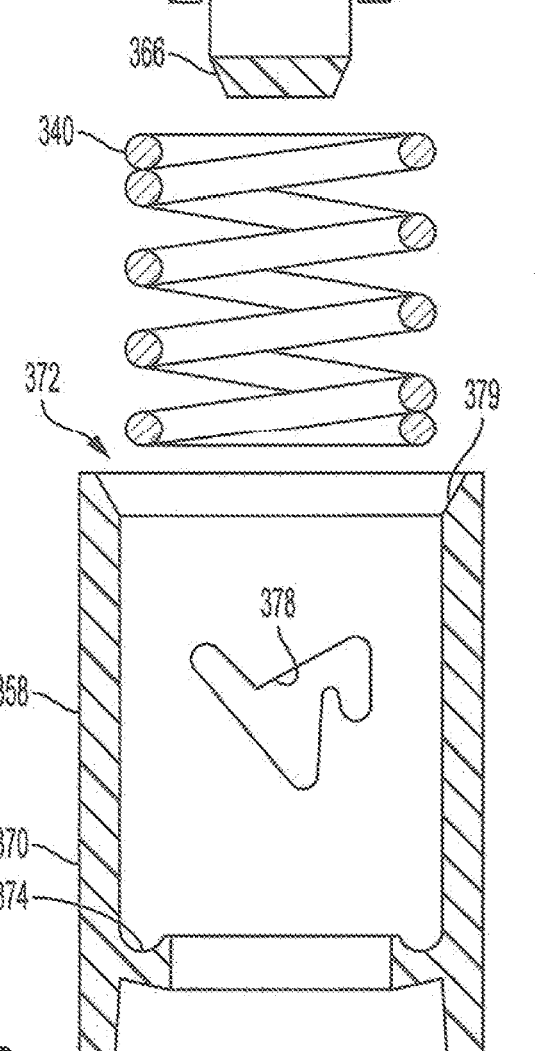

FIG. 9 illustrates an exploded longitudinal section view of the lock-out mechanism 336, including the shuttle 360, the resilient member 340, and the shuttle holder 358. The shuttle 360 includes a shuttle body 362 that defines a shuttle opening 364 for receiving the discharge element 334 of the drug delivery device 304 (shown in FIG. 8), and a base portion 366 for coupling to the discharge element 334 is disposed below the shuttle opening 364. The shuttle body

362 also includes a shuttle flange 367 for coupling to the resilient member 340 and a plurality of stop elements 368 for inhibiting the shuttle 360 from detaching from the shuttle holder 358. The shuttle holder 358 includes a holder body 370 that defines a passageway 372 for receiving the resilient member 340 and the shuttle 360. The holder body 370 also includes a holder flange 374 for coupling to the resilient member 340 and engaging the stop elements 368 of the shuttle 360.

With continued reference to FIG. 9, the lock-out mechanism 336 also includes a radially-extending pin 376 and asymmetric slot 378 for translatably receiving the pin 376, which together may be referred to as a pin-and-slot connection, that inhibit reclosing the drug delivery system 300. In some embodiments and as illustrated, the shuttle 360 includes the pin 376 and the shuttle holder 358 includes the slot 378. In other embodiments, the shuttle 360 may include the slot 378 and the shuttle holder 358 may include the pin 376. In some embodiments and as illustrated, the lock-out mechanism 336 includes a single pin-and-slot connection (that is, one pin 376 translatably received in one slot 378). In other embodiments, the lock-out mechanism 336 includes a plurality of pin-and-slot connections (that is, a plurality of pins 376 each received in a different slot 378). As a specific example, the lock-out mechanism 336 includes two pin-and-slot connections to balance forces applied to the resilient member 340.

To facilitate assembly, the shuttle holder 358 may deform to permit insertion of the shuttle 360 and accommodate the pin 376 (or pins 376). As the pin 376 is inserted, a taper 379 at the end of the passageway 372 provide a lead-in for the pin 376 to temporarily urge the walls of the shuttle holder 358 to deform to provide room for the pin 376 during assembly.

Figure 10:
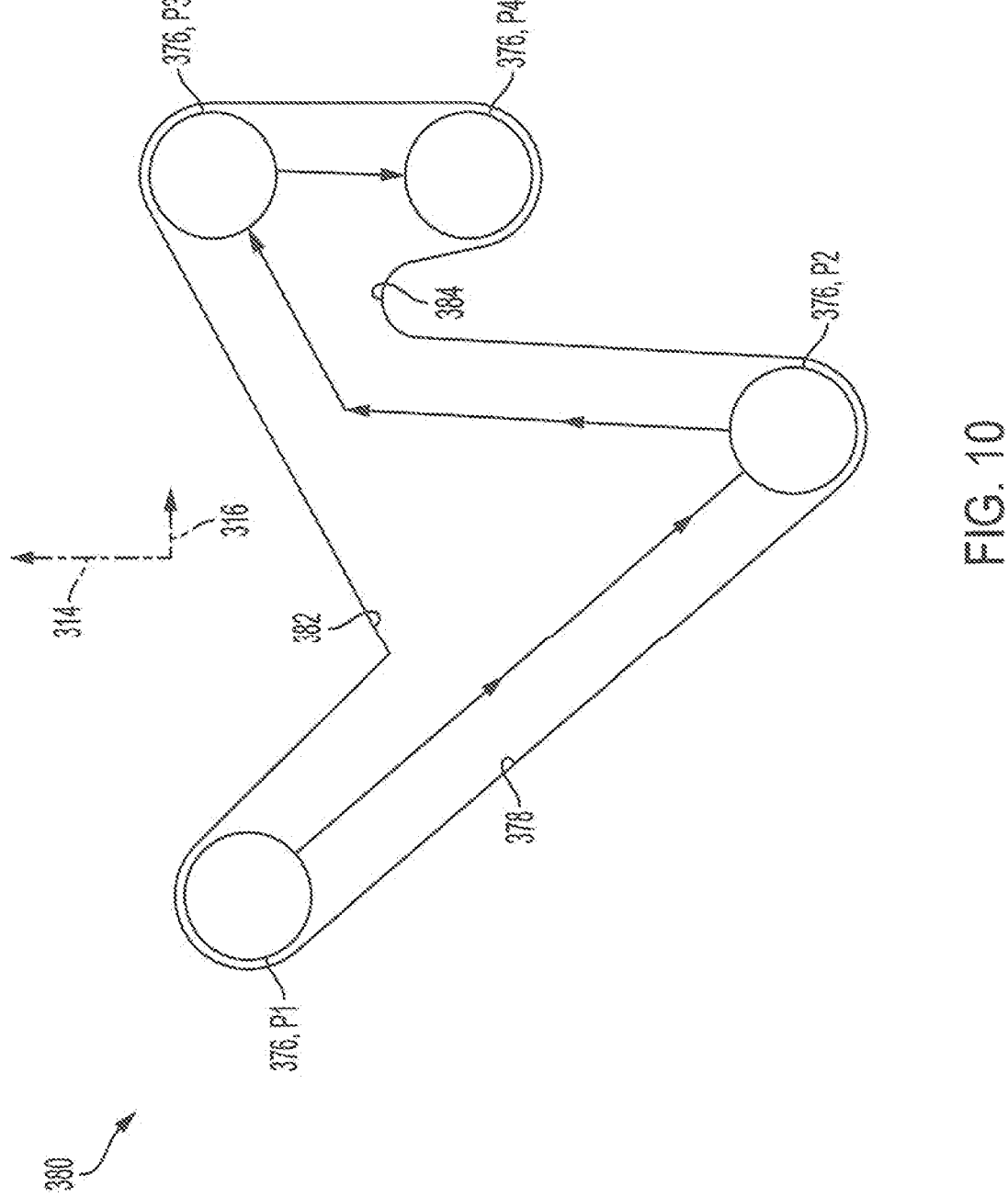
FIG. 10 illustrates a travel path of a pin in a slot of the lock-out mechanism of FIG. 9.
Figure 12:
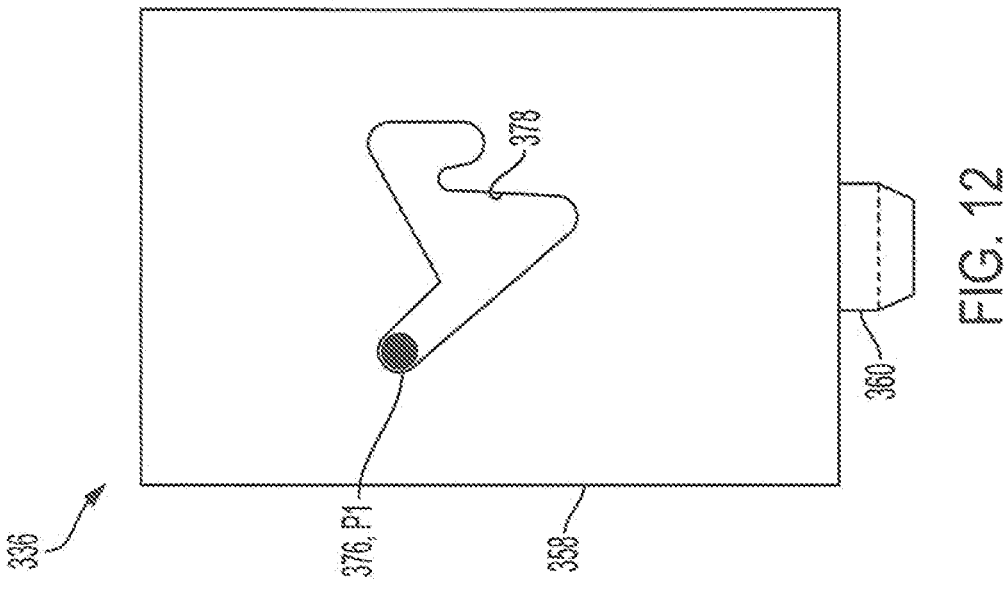
FIG. 12 is a side view of the lock-out mechanism of the drug delivery system of FIG. 8 before receiving the drug delivery device.
Figure 11:
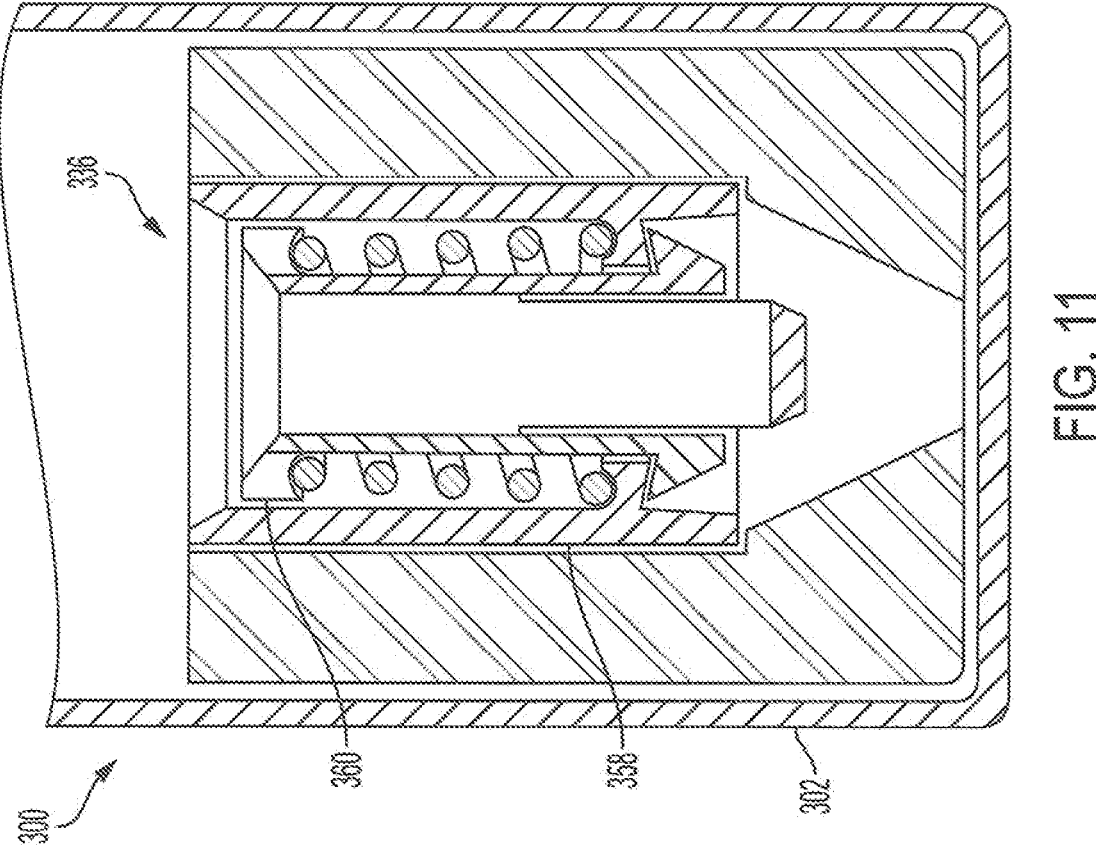
FIG. 11 is a partial longitudinal section side view of the housing and the lock-out mechanism of the drug delivery system of FIG. 8 before receiving the drug delivery device.
Figure 14:
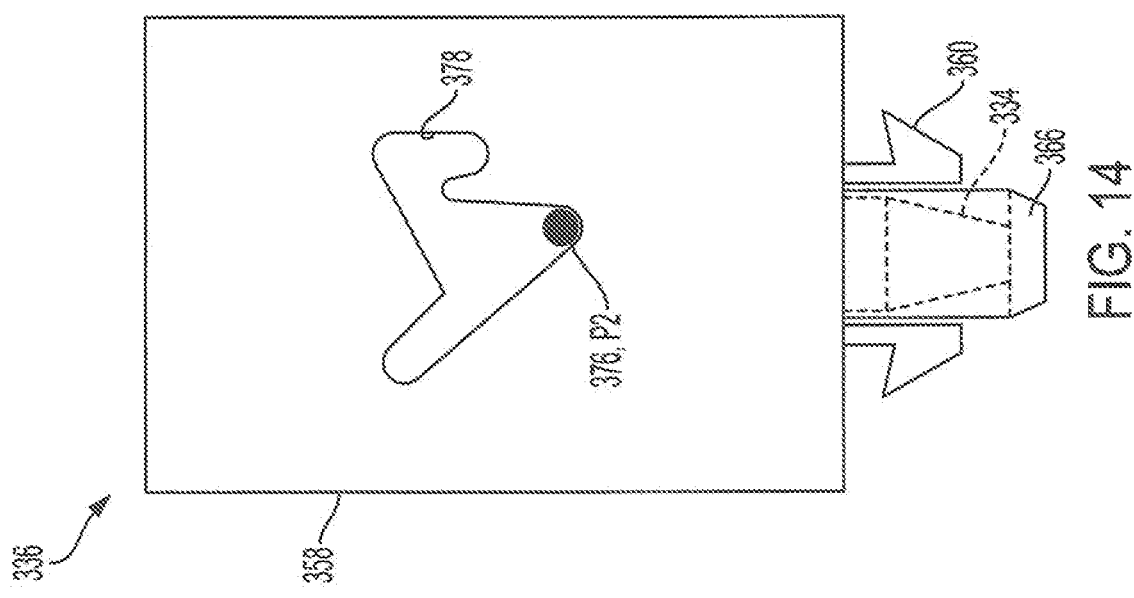
FIG. 14 is a side view of the lock-out mechanism of the drug delivery system of FIG. 8 upon receiving the drug delivery device.
Figure 13:
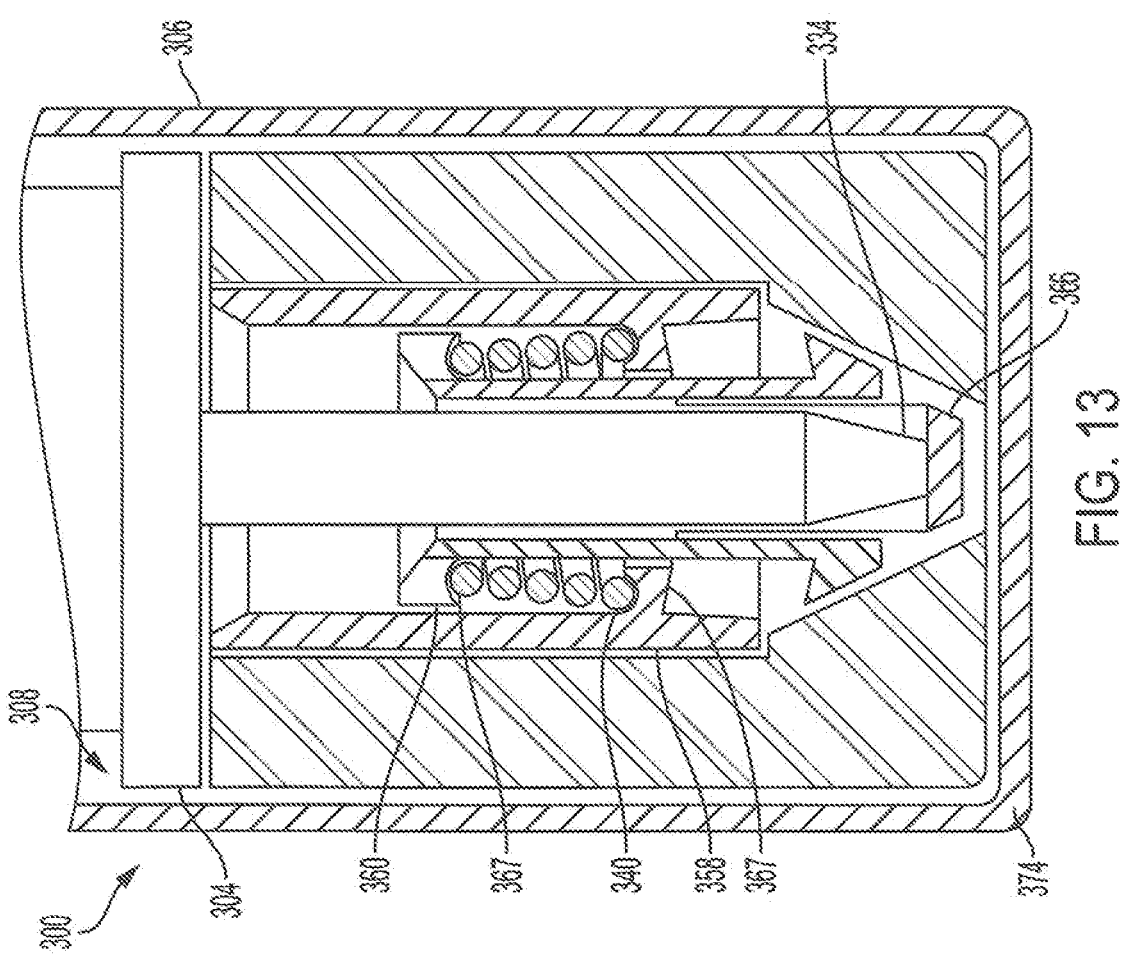
FIG. 13 is a partial longitudinal section side view of the housing and the lock-out mechanism of the drug delivery system of FIG. 8 upon receiving the drug delivery device.

FIG. 10 illustrates the pin-and-slot connection and a travel path 380 of the pin 376 in the slot 378 as the shuttle 360 moves relative to the shuttle holder 358 (shown elsewhere). With continued reference to FIG. 10 and additional reference to FIGS. 11-12, before the housing 302 receives the drug delivery device 304 (shown elsewhere) and the lock-out mechanism 336 receives the discharge element 334 of the drug delivery device 304 (shown elsewhere), the pin 376 of the shuttle 360 occupies a pre-assembly position P1 in the slot 378 of the shuttle holder 358.

With reference to FIGS. 8, 10, and 13-14, placing the drug delivery device 304 in the main chamber 308 and closing the cover 310 against the main body 306 causes the ribs 356 of the cover 310 (see FIG. 8) to push the drug delivery device 304 further into the main chamber 308, or to a storage position. This action causes the discharge element 334 of the drug delivery device 304 (see FIG. 13) to engage the base portion 366 of the shuttle 360, and the drug delivery device 304 thereby pushes the shuttle 360 further into the main chamber 308 relative to the shuttle holder 358. As a result, the pin 376 translates to an initial position P2 in the slot 378. Due to the shape of the slot 378, the pin 376 translates diagonally relative to the longitudinal axis 314 (FIG. 10), or along the longitudinal axis 314 and perpendicular to the longitudinal axis 314 as the shuttle 360 rotates relative to the shuttle holder 358, when moving to the initial position P2. In addition, the resilient member 340 is compressed between the shuttle flange 367 and the holder flange 374. The drug delivery system 300 may be provided to a user when the cover 310 is closed, the drug delivery device 304 is in the storage position, and the pin 376 is in the initial position P2.

Figure 15:
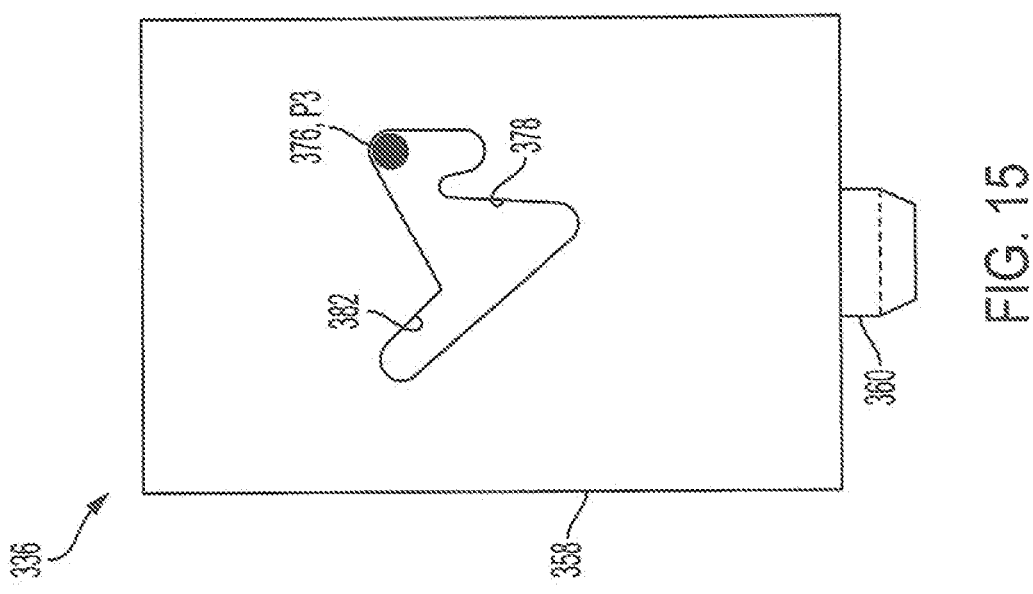
FIG. 15 is a side view of the lock-out mechanism of the drug delivery system of FIG. 8 upon opening a cover of the system and deploying the drug delivery device.

Opening the cover 310 causes the ribs 356 (see FIG. 8) to disengage the drug delivery device 304, which permits to the resilient member 340 to unload and thereby causes the shuttle 360 to translate toward the main opening 312 relative to the shuttle holder 358 until the stop elements 368 of the shuttle 360 contact the holder flange 374 of the shuttle holder 358. As a result, the drug delivery device 304 moves relative to the main body 306 to a deployed position, and the drug delivery device 304 may be removed from the housing 302 for discharging the drug therefrom. With reference to FIGS. 10 and 15, the above translation of the shuttle 360 relative to the shuttle holder 358 causes the pin 376 to translate away from the initial position P2 and toward a first lock-out position P3. That is, the pin 376 translates along the longitudinal axis 314 and perpendicular to the longitudinal axis 314 as the shuttle 360 rotates relative to the shuttle holder 358. Further, the pin 376 does not return to the pre-assembly position P1 due to the shape of the slot 378, specifically the presence of a first apex 382 disposed longitudinally and circumferentially between the initial position P2 and the pre-assembly position P1.

Figure 16:
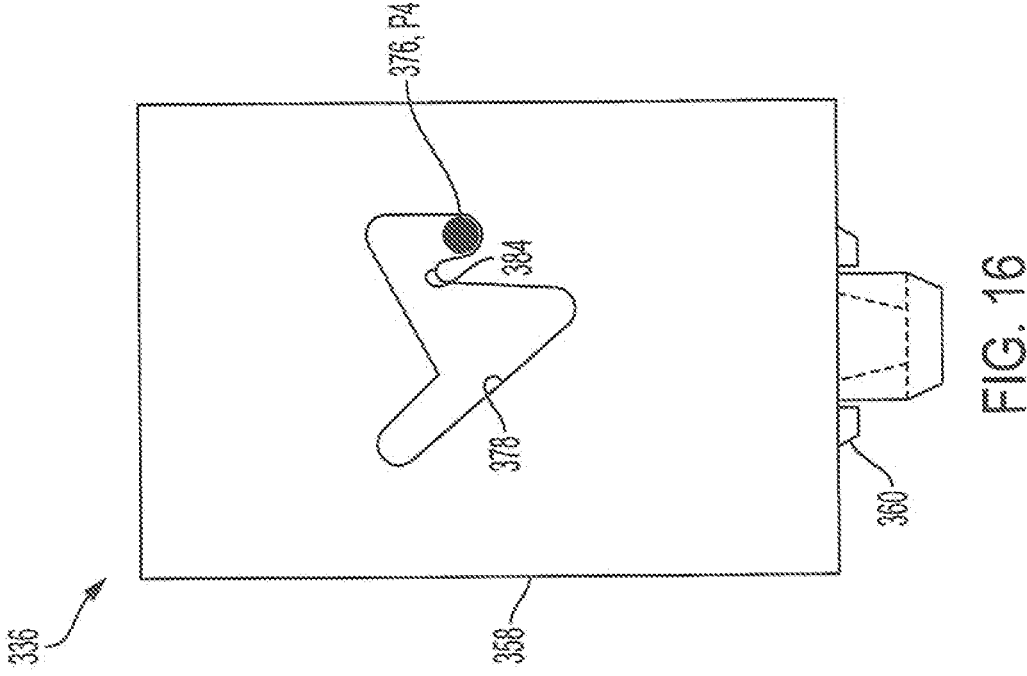
FIG. 16 is a side view of the lock-out mechanism of the drug delivery system of FIG. 8 upon replacing the drug delivery device in the housing and attempting to reclose the cover.

After use, the drug delivery device 304 may be replaced in the main body 306 in the deployed position. Attempting to reclose the cover 310 on the main body 306 causes the ribs 356 of the cover 310 (see FIG. 8) to push the drug delivery device 304, which causes the discharge element 334 of the drug delivery device 304 (see FIG. 13) to push the base portion 366 of the shuttle 360, and the shuttle 360 thereby moves further into the main chamber 308 relative to the shuttle holder 358. With reference to FIGS. 10 and 16, this translation of the shuttle 360 relative to the shuttle holder 358 causes the pin 376 to translate away from the first lock-out position P3 and toward a second lock-out position P4. The pin 376 does not return to the initial position P2 due to the shape of the slot 378, specifically the presence of a second apex 384 longitudinally and circumferentially between the first lock-out position P3 and the initial position P2. The second lock-out position P4 is disposed proximate the first lock-out position P3 along the longitudinal axis 314, and the shuttle 360 does not rotate relative to the shuttle holder 358 when the pin 376 moves from the first lock-out position P3 to the second lock-out position P4. As a result, the drug delivery device 304 does not enter the main chamber 308 a distance sufficient to permit the cover 310 to reclose on the main body 306.

Delivery systems according to some embodiments of the present disclosure may include other types of devices, products, or objects instead of drug delivery devices. For example, delivery systems according to some embodiments of the present disclosure may include various types of disposable/one time use products, such as syringes, applicators, suction catheters, dental carpules, initially sterile/one time use surgical devices, and the like.

While embodiments of the invention have been described as having exemplary designs, the embodiments of the present disclosure may be further modified within the spirit and scope of this disclosure. This application is therefore intended to cover any variations, uses, or adaptations of the disclosed embodiments using its general principles.

Various aspects are described in this disclosure, which include, but are not limited to, the following aspects:

1. A drug delivery system, comprising: a drug delivery device carrying and configured to deliver a drug; a housing, comprising: a main body comprising a chamber carrying the drug delivery device and an opening coupled to the chamber; a cover coupled to the main body, the cover being movable relative to the main body from a closed position to an open position, in the closed position the cover obscuring the opening and thereby inhibiting egress of the drug delivery device from the chamber via the opening, and in the open position the cover permitting egress of the drug delivery device from the chamber via the opening; and a lock-out mechanism carried by the housing, the lock-out mechanism configured to inhibit the cover from returning to the closed position after moving to the open position.

2. The drug delivery system of aspect 1, wherein the lock-out mechanism is movable from an initial position to a lock-out position, the lock-out mechanism occupying the initial position when the cover occupies the closed position, and the lock-out mechanism occupying the lock-out position when the cover occupies the open position to inhibit the cover from returning to the closed position.

3. The drug delivery system of aspect 2, wherein the lock-out mechanism extends through the opening in the lock-out position.

4. The drug delivery system of aspect 2, wherein the chamber is a main chamber and the opening is a main opening, the cover comprises a cover chamber carrying the lock-out mechanism and a cover opening coupled to the cover chamber, and wherein the lock-out mechanism extends through the cover opening in the lock-out position.

5. The drug delivery system of any one of aspects 1-4, wherein the lock-out mechanism is carried within the chamber.

6. The drug delivery system of any one of aspects 1-5, wherein the chamber is a main chamber, and wherein the cover comprises a cover chamber, the lock-out mechanism being carried within the cover chamber.

7. The drug delivery system of any one of aspects 1-6, wherein the lock-out mechanism comprises a resilient member configured to interfere with the cover to inhibit the cover from returning to the closed position after moving to the open position.

8. The drug delivery system of any one of aspects 1-7, wherein the lock-out mechanism comprises a resilient member configured to interfere with the main body to inhibit the cover from returning to the closed position after moving to the open position.

9. The drug delivery system of any one of aspects 1-8, wherein the drug delivery device is movable relative to main body from a storage position to a deployed position, in the closed position the cover holding the drug delivery device in the storage position, and in the open position the cover permitting the lock-out mechanism to urge the drug delivery device to the deployed position.

10. The drug delivery system of aspect 9, wherein the lock-out mechanism is configured to inhibit the drug delivery device from returning to the storage position after moving to the deployed position and thereby inhibit the cover from returning to the closed position after moving to the open position.

11. The drug delivery system of aspect 9, wherein the lock-out mechanism comprises: a shuttle carrying the drug delivery device; a shuttle holder translatably carrying the shuttle; and a resilient member coupling the shuttle and the shuttle holder, the resilient member urging the shuttle and the drug delivery device away from the storage position and toward the deployed position.

12. The drug delivery system of aspect 11, wherein at least one of: (i) the lock-out mechanism further comprises a pin-and-slot connection, the pin-and-slot connection coupling the shuttle to the shuttle holder and configured to inhibit the drug delivery device from returning to the storage position after moving to the deployed position, and the pin-and-slot connection thereby configured to inhibit the cover from returning to the closed position after moving to the open position; or (ii) the system further comprises an annular desiccant element configured to receive a portion of the drug delivery device and the shuttle holder, wherein said portion of the drug delivery device and the shuttle holder are in a coaxial relationship and the shuttle holder is at least one of rotationally and axially locked relative to the annular desiccant.

13. A drug delivery system, comprising: a drug delivery device carrying and configured to deliver a drug; a housing, comprising: a first housing portion comprising a chamber carrying the drug delivery device and an opening coupled to the chamber; a second housing portion coupled to the first housing portion, the second housing portion initially obscuring the opening and thereby inhibiting egress of the drug delivery device from the chamber via the opening, and the second housing portion being movable relative to the first housing portion to open the housing and permit egress of the drug delivery device from the chamber via the opening; and a lock-out mechanism carried by the housing, the lock-out mechanism configured to inhibit the housing from reclosing after being opened.

14. The drug delivery system of aspect 13, wherein the lock-out mechanism comprises a resilient member configured to interfere with the second housing portion to inhibit the housing from reclosing after being opened.

15. The drug delivery system of any one of aspects 13-14, wherein the lock-out mechanism comprises a resilient member configured to interfere with the first housing portion to inhibit the housing from reclosing after being opened.

16. A drug delivery system, comprising: a drug delivery device carrying and configured to deliver a drug; a housing, comprising: a main body comprising a chamber carrying the drug delivery device and an opening coupled to the chamber; a cover coupled to the main body, the cover being movable relative to the main body from a closed position to an open position, in the closed position the cover obscuring the opening and thereby inhibiting egress of the drug delivery device from the chamber via the opening, and in the open position the cover permitting egress of the drug delivery device from the chamber via the opening; and a lock-out mechanism carried by the housing, the lock-out mechanism being movable from an initial position to a lock-out position, the lock-out mechanism occupying the initial position when the cover occupies the closed position, the lock-out mechanism occupying the lock-out position when the cover occupies the open position, and in the lock-out position the lock-out mechanism causing one of the drug delivery device and the lock-out mechanism to be disposed outwardly of the housing and thereby inhibit the cover from returning to the closed position.

17. The drug delivery system of aspect 16, wherein the lock-out mechanism comprises a resilient member, in the lock-out position the resilient member being disposed outwardly of the housing and thereby inhibiting the cover from returning to the closed position.

18. The drug delivery system of aspect 17, wherein the resilient member is loaded in the initial position and unloaded in the lock-out position.

19. The drug delivery system of any one of aspects 16-18, wherein in the lock-out position the drug delivery device extends through the opening and thereby inhibits the cover from returning to the closed position.

20. The drug delivery system of aspect 19, wherein the lock-out mechanism comprises a resilient member, the resilient member being loaded in the initial position and unloaded in the lock-out position, and in the lock-out position the resilient member urging the drug delivery device to extend through the opening and thereby inhibiting the cover from returning to the closed position.

What is claimed is:

1. A drug delivery system, comprising:
a drug delivery device carrying and configured to deliver a drug;
a housing, comprising:
a main body comprising a chamber carrying the drug delivery device and an opening coupled to the chamber;
a cover hingedly coupled to the main body, the cover being movable relative to the main body from a closed position to an open position, in the closed position the cover obscuring the opening and thereby inhibiting egress of the drug delivery device from the chamber via the opening, and in the open position the cover permitting egress of the drug delivery device from the chamber via the opening; and
a lock-out mechanism carried by the housing, the lock-out mechanism being movable from an initial position to a lock-out position, the lock-out mechanism occupying the initial position when the cover occupies the closed position, the lock-out mechanism occupying the lock-out position when the cover occupies the open position, and in the lock-out position the lock-out mechanism causing one of the drug delivery device and the lock-out mechanism to be disposed outwardly of the housing and thereby inhibit the cover from returning to the closed position.

2. The drug delivery system of claim 1, wherein the lock-out mechanism extends through the opening in the lock-out position.

3. The drug delivery system of claim 1, wherein the chamber is a main chamber and the opening is a main opening, the cover comprises a cover chamber carrying the lock-out mechanism and a cover opening coupled to the cover chamber, and wherein the lock-out mechanism extends through the cover opening in the lock-out position.

4. The drug delivery system of claim 1, wherein the lock-out mechanism is carried within the chamber.

5. The drug delivery system of claim 1, wherein the chamber is a main chamber, and wherein the cover comprises a cover chamber, the lock-out mechanism being carried within the cover chamber.

6. The drug delivery system of claim 1, wherein the lock-out mechanism comprises a resilient member configured to interfere with the cover to inhibit the cover from returning to the closed position after moving to the open position.

7. The drug delivery system of claim 1, wherein the lock-out mechanism comprises a resilient member configured to interfere with the main body to inhibit the cover from returning to the closed position after moving to the open position.

8. The drug delivery system of claim 1, wherein the drug delivery device is movable relative to main body from a storage position to a deployed position, in the closed position the cover holding the drug delivery device in the storage position, and in the open position the cover permitting the lock-out mechanism to urge the drug delivery device to the deployed position.

9. The drug delivery system of claim 8, wherein the lock-out mechanism is configured to inhibit the drug delivery device from returning to the storage position after moving to the deployed position and thereby inhibit the cover from returning to the closed position after moving to the open position.

10. The drug delivery system of claim 8, wherein the lock-out mechanism comprises:
a shuttle carrying the drug delivery device;
a shuttle holder translatably carrying the shuttle; and
a resilient member coupling the shuttle and the shuttle holder, the resilient member urging the shuttle and the drug delivery device away from the storage position and toward the deployed position.

11. The drug delivery system of claim 10, wherein at least one of: (i) the lock-out mechanism further comprises a pin-and-slot connection, the pin-and-slot connection coupling the shuttle to the shuttle holder and configured to inhibit the drug delivery device from returning to the storage position after moving to the deployed position, and the pin-and-slot connection thereby configured to inhibit the cover from returning to the closed position after moving to the open position; or (ii) the system further comprises an annular desiccant element configured to receive a portion of the drug delivery device and the shuttle holder, wherein said portion of the drug delivery device and the shuttle holder are in a coaxial relationship and the shuttle holder is at least one of rotationally and axially locked relative to the annular desiccant.

12. The drug delivery system of claim 1, wherein the lock-out mechanism comprises a resilient member, in the lock-out position the resilient member being disposed outwardly of the housing and thereby inhibiting the cover from returning to the closed position.

13. The drug delivery system of claim 12, wherein the resilient member is loaded in the initial position and unloaded in the lock-out position.

14. The drug delivery system of claim 1, wherein in the lock-out position the drug delivery device extends through the opening and thereby inhibits the cover from returning to the closed position.

15. The drug delivery system of claim 14, wherein the lock-out mechanism comprises a resilient member, the resilient member being loaded in the initial position and unloaded in the lock-out position, and in the lock-out position the resilient member urging the drug delivery device to extend through the opening and thereby inhibiting the cover from returning to the closed position.

* * * * *